(12) United States Patent
Kapec et al.

(10) Patent No.: US 10,028,731 B2
(45) Date of Patent: Jul. 24, 2018

(54) BARRIER APPLICATION DEVICE (71) Applicant: Genzyme Corporation, Cambridge, MA (US)

(72) Inventors: Jeffrey Kapec, Westport, CT (US); Kazuna Tanaka, Cos Cob, CT (US); Yukiko Naoi, New York, NY (US); Joseph Jeffrey Kablik, Tyngsboro, MA (US)

(73) Assignee: GENZYME CORPORATION, Cambridge, MA (US)

( * ) Notice: Subject to any disclaimer, the term of this patent is extended or adjusted under 35 U.S.C. 154(b) by 746 days.

(21) Appl. No.: 14/077,893

(22) Filed: Nov. 12, 2013

(65) Prior Publication Data

US 2015/0128959 A1    May 14, 2015

(51) Int. Cl.
*A61B 17/00* (2006.01)
*A61B 17/29* (2006.01)
(Continued)

(52) U.S. Cl.
CPC ............... *A61B 17/00234* (2013.01); *A61B 2017/00424* (2013.01); *A61B 2017/00429* (2013.01);
(Continued)

(58) Field of Classification Search
CPC . A61B 17/0218; A61B 17/0281; A61B 19/26; A61B 17/3417; A61B 2017/00557;
(Continued)

(56) References Cited

U.S. PATENT DOCUMENTS 4,874,375 A * 10/1989 Ellison ............... A61B 17/0218
600/204
5,156,613 A   10/1992 Sawyer et al.
(Continued)

FOREIGN PATENT DOCUMENTS

CA    2581783    10/2004
CA    2681325    9/2013
(Continued)

OTHER PUBLICATIONS

US 5,263,989, 11/1993, Phillips (withdrawn)
(Continued)

*Primary Examiner* — Ophelia A Hawthorne
(74) *Attorney, Agent, or Firm* — Jeremy P. Bond (57) ABSTRACT

Described is a barrier application device comprising a handle, an introducer assembly slidably and rotatably coupled to the handle, a beam assembly coupled to a distal end of the handle, and a flag coupled to the beam assembly. A method of using a barrier application device comprises providing a device comprising a handle, an introducer assembly slidably and rotatably coupled to the handle, a beam assembly coupled to a distal end of the handle, and a flag coupled to the beam assembly, and placing a barrier on the flag, sliding the introducer assembly along the handle from a retracted position to an extended position at least partially covering the beam assembly, and rotating the handle relative to the introducer assembly until the flag and the barrier are wound around the beam assembly.

24 Claims, 7 Drawing Sheets

(51) Int. Cl.
*A61F 2/00* (2006.01)
*A61B 90/00* (2016.01)

(52) U.S. Cl.
CPC ........... *A61B 2017/00455* (2013.01); *A61B 2017/2927* (2013.01); *A61B 2090/0816* (2016.02); *A61F 2/0063* (2013.01); *A61F 2002/0072* (2013.01)

(58) Field of Classification Search
CPC ...... A61B 17/00234; A61B 2090/0816; A61B 2017/00424; A61B 2017/00429; A61B 2017/00455; A61B 2017/2927; A61B 19/08; A61B 19/088; A61B 19/081; A61B 2019/085; A61F 2/0063; A61F 2002/0072; A61F 15/005
See application file for complete search history.

(56) References Cited

U.S. PATENT DOCUMENTS

| | | | |
|---|---|---|---|
| 5,195,958 | A | 3/1993 | Phillips |
| 5,304,176 | A | 4/1994 | Phillips |
| 5,304,187 | A * | 4/1994 | Green ................... A61F 2/0063 604/13 |
| 5,324,254 | A | 6/1994 | Phillips |
| 5,334,140 | A | 8/1994 | Phillips |
| 5,370,650 | A * | 12/1994 | Tovey ................. A61B 17/0057 128/899 |
| 5,380,2777 | | 1/1995 | Phillips |
| 5,464,403 | A | 11/1995 | Kieturakis et al. |
| 5,503,623 | A | 4/1996 | Tilton |
| 5,634,931 | A | 6/1997 | Kugel |
| 5,669,934 | A | 9/1997 | Sawyer et al. |
| 5,681,342 | A | 10/1997 | Benchetrit |
| 5,690,675 | A | 11/1997 | Sawyer et al. |
| 5,749,895 | A | 5/1998 | Sawyer et al. |
| 5,766,157 | A | 6/1998 | Tilton |
| 5,785,677 | A | 7/1998 | Auweiler |
| 5,791,352 | A | 8/1998 | Reich et al. |
| 5,797,899 | A | 8/1998 | Tilton |
| 5,824,015 | A | 10/1998 | Sawyer |
| 5,919,184 | A | 7/1999 | Tilton |
| 5,931,165 | A | 8/1999 | Reich et al. |
| 5,957,939 | A | 9/1999 | Heaven et al. |
| 6,010,495 | A | 1/2000 | Tilton |
| 6,033,426 | A | 3/2000 | Kaji |
| 6,042,592 | A | 3/2000 | Schmitt et al. |
| 6,110,181 | A | 8/2000 | Yu |
| 6,183,485 | B1 | 2/2001 | Thomason et al. |
| 6,193,731 | B1 | 2/2001 | Oppeit et al. |
| 6,375,662 | B1 | 4/2002 | Schmitt et al. |
| 6,416,506 | B1 * | 7/2002 | Tilton, Jr. ........ A61B 17/00234 606/1 |
| 6,478,803 | B1 * | 11/2002 | Kapec ............. A61B 17/00234 606/151 |
| 6,641,575 | B1 | 11/2003 | Lonky et al. |
| 6,669,706 | B2 | 12/2003 | Schmitt et al. |
| 6,676,639 | B1 | 1/2004 | Ternstrom |
| 6,695,815 | B2 | 2/2004 | Moenning |
| 6,723,088 | B2 | 4/2004 | Gaskill et al. |
| 6,966,916 | B2 | 11/2005 | Kumar |
| 7,081,135 | B2 | 7/2006 | Smith et al. |
| 7,105,009 | B2 | 9/2006 | Johnson et al. |
| 7,320,693 | B2 | 1/2008 | Pollack et al. |
| 7,390,317 | B2 | 6/2008 | Taylor et al. |
| 7,429,259 | B2 | 9/2008 | Cadeddu et al. |
| 7,501,802 | B2 | 9/2009 | Johnson et al. |
| 7,582,098 | B2 | 9/2009 | Gobel |
| 7,608,082 | B2 | 10/2009 | Cuevas et al. |
| 7,651,478 | B2 | 1/2010 | Brustad |
| 7,691,103 | B2 | 4/2010 | Fernandez et al. |
| 7,846,171 | B2 | 12/2010 | Kullas et al. |
| 7,867,222 | B1 | 1/2011 | Tilton et al. |
| 7,947,054 | B2 * | 5/2011 | Eldar ............... A61B 17/00234 606/151 |
| 2002/0049413 | A1 | 4/2002 | Moenning |
| 2002/0052612 | A1 | 5/2002 | Schmitt et al. |
| 2003/0149443 | A1 | 8/2003 | Gaskill et al. |
| 2004/0034339 | A1 | 2/2004 | Stoller et al. |
| 2004/0092970 | A1 | 5/2004 | Xavier et al. |
| 2004/0092989 | A1 | 5/2004 | Kumar |
| 2004/0093018 | A1 | 5/2004 | Johnson et al. |
| 2004/0106942 | A1 | 6/2004 | Taylor et al. |
| 2004/0111061 | A1 | 6/2004 | Curran |
| 2004/0249457 | A1 | 12/2004 | Smith et al. |
| 2005/0043746 | A1 | 2/2005 | Pollak et al. |
| 2005/0165449 | A1 | 7/2005 | Cadeddu et al. |
| 2005/0216028 | A1 | 9/2005 | Hart et al. |
| 2006/0129154 | A1 | 6/2006 | Shipp et al. |
| 2006/0149305 | A1 | 7/2006 | Cuevas et al. |
| 2006/0200004 | A1 | 9/2006 | Wilk |
| 2006/0264991 | A1 | 11/2006 | Johnson et al. |
| 2006/0264998 | A1 | 11/2006 | Johnson et al. |
| 2007/0049860 | A1 | 3/2007 | Seminara |
| 2007/0073337 | A1 | 3/2007 | Abbott et al. |
| 2007/0112361 | A1 * | 5/2007 | Schonholz ....... A61B 17/00234 606/151 |
| 2007/0233606 | A1 | 10/2007 | Brustad |
| 2007/0255273 | A1 | 11/2007 | Fernandez et al. |
| 2008/0058852 | A1 | 3/2008 | Ihde |
| 2008/0097468 | A1 | 4/2008 | Adams et al. |
| 2008/0097470 | A1 | 4/2008 | Gruber et al. |
| 2008/0121553 | A1 | 5/2008 | Gobel |
| 2008/0146882 | A1 | 6/2008 | Cropper et al. |
| 2008/0200934 | A1 | 8/2008 | Fox |
| 2009/0005795 | A1 | 1/2009 | Glap |
| 2009/0043246 | A1 | 2/2009 | Dominguez |
| 2009/0069837 | A1 | 3/2009 | Bonadio et al. |
| 2009/0137877 | A1 | 5/2009 | Minnelli et al. |
| 2009/0187079 | A1 | 7/2009 | Albrecht et al. |
| 2009/0259185 | A1 | 10/2009 | Okoniewski |
| 2009/0270688 | A1 | 10/2009 | Duke et al. |
| 2010/0063452 | A1 | 3/2010 | Edelman et al. |
| 2010/0081881 | A1 | 4/2010 | Murray et al. |
| 2010/0211000 | A1 | 8/2010 | Killion et al. |
| 2010/0280437 | A1 | 11/2010 | Murr |
| 2010/0305587 | A1 | 12/2010 | Straehnz |
| 2011/0022065 | A1 | 1/2011 | Shipp |
| 2011/0029003 | A1 | 2/2011 | Lavigne et al. |
| 2011/0034935 | A1 | 2/2011 | Kleyman |
| 2011/0054485 | A1 | 3/2011 | Kullas et al. |
| 2011/0079627 | A1 | 4/2011 | Cardinale et al. |
| 2011/0082343 | A1 | 4/2011 | Okoniewski |
| 2011/0105848 | A1 * | 5/2011 | Sadovsky .......... A61B 17/0218 600/204 |
| 2011/0124967 | A1 | 5/2011 | Morgan et al. |

FOREIGN PATENT DOCUMENTS

| | | |
|---|---|---|
| CN | 2910140 | 6/2007 |
| CN | 201026203 | 2/2008 |
| CN | 101775982 | 7/2010 |
| DE | 102009034251 | 1/2011 |
| EP | 0581036 | 2/1994 |
| EP | 2266476 | 10/2006 |
| JP | 2002360582 | 12/2002 |
| JP | 2006280848 | 10/2006 |
| JP | 2006296666 | 11/2006 |
| RU | 2150897 | 6/2000 |
| RU | 2169528 | 6/2001 |
| RU | 2241392 | 12/2004 |
| RU | 2337636 | 11/2008 |
| WO | WO 92/14513 | 9/1992 |
| WO | WO 96/07355 | 3/1996 |
| WO | WO 96/07356 | 3/1996 |
| WO | WO 97/36622 | 10/1997 |
| WO | WO 98/16165 | 4/1998 |
| WO | WO 2001/026563 | 4/2001 |
| WO | WO 01/89390 | 11/2001 |
| WO | WO 2004/080348 | 9/2004 |
| WO | WO 2006/041474 | 4/2006 |
| WO | WO 2007/044808 | 4/2007 |
| WO | WO 2008/068405 | 6/2008 |

(56) References Cited

FOREIGN PATENT DOCUMENTS

| WO | WO 2010/045702 | 4/2010 |
| WO | WO 2010/050243 | 5/2010 |
| WO | WO 2010/087330 | 8/2010 |

OTHER PUBLICATIONS

Hakko Co. Ltd, Instructions for Use: A.P.S. Introducer, May 31, 2007, pp. 1-3, 3rd Edition, Tokyo, Japan.
International Search Report and Written Opinion for Application No. PCT/US2014/064964, dated Feb. 13, 2015, 13 pages.

* cited by examiner

BARRIER APPLICATION DEVICE

BACKGROUND

After a surgical procedure, organs and/or tissues adjacent to a surgical site may adhere to the surgical site by fibrous bands of tissue know as adhesions. Adhesions may result in delayed healing, post-operative pain and/or infection, and potentially a need for further surgical intervention. Thus, there is a need for a barrier for preventing adhesion to the surgical site.

Adhesion formation can be prevented or limited by providing a physical barrier between the traumatized surgical site and adjacent organs and/or tissue, The physical barrier can be applied to sites of potentially adhesiogenic tissue and organ structures to serve as a temporary barrier separating opposing tissue/organ surfaces. These barriers are often provided as films that are applied at the conclusion of the surgical procedure.

While such film-like barriers would be useful, it may be difficult to apply such a barrier during a surgical procedure. For example, during laparoscopic procedures the surgery is performed by using a camera that is mounted on laparoscope that is inserted through a small surgical port called a trocar. The surgical site is viewed on a monitor and surgical instruments access the site through additional trocars. Conventional trocars vary in diameter from 5 mm to 12 mm in diameter. To minimize trauma and scarring both the surgeon and patient prefer to use as small a trocar as possible. As a consequence it becomes challenging to be able to insert a film-like barrier through a trocar and a deliver it to a surgical site while viewing on a monitor. For example, the film-like barrier will need to be introduced into the body in a collapsed state and then expanded back to its original form. It may be difficult to collapse the barrier (e.g., depending on its material properties, size and/or shape) and/or expand (e.g., depending on its collapsed orientation/configuration, if it comes into contact with liquid, etc.).

In addition, there are other factors that could complicate the delivery of a film-like barrier in a laparoscopic procedure. For example, due to the confined spaces in laparoscopic surgery, the film-like barrier may adhere to unintended organs and/or tissue. In addition, the film-like barrier may be sticky when it comes in contact with a liquid such as blood or saline used for irrigation causing the film-like barrier to inadvertently adhere to the trocar, unintended tissue/organ or itself. Multiple barriers may be needed to adequately cover the surgical site. Therefore, there exists a need for an improved barrier application device for effectively deploying a barrier at a surgical site.

SUMMARY OF THE INVENTION

In an exemplary embodiment, a device according to the present invention comprises a handle, an introducer assembly slidably and rotatably coupled to the handle, a beam assembly coupled to a distal end of the handle, and a flag coupled to the beam assembly. The device may be utilized to deploy a barrier at a surgical site.

In an exemplary embodiment, the handle includes a grip portion and a shaft portion. The grip portion may include a frictional surface. The grip portion may include an orientation indicator. The orientation indicator may include at least one of a projection, a recess, a symbol and a color.

In an exemplary embodiment, the introducer assembly includes an introducer tube and an introducer stop. The introducer tube may include a distal end with a distal opening that is contiguous with a slot formed along at least a portion of a length of the introducer tube. The distal end may be beveled. The introducer stop may have an external diameter greater than an external diameter of the introducer tube.

In an exemplary embodiment, the device further comprises a sleeve coupled to a distal end of the handle.

In an exemplary embodiment, the device further comprises a flex joint coupled to the beam assembly and the handle. The flex joint may be biased in a non-deflected state coaxial with the handle and movable to a deflected state at an angle relative to the handle. The angle may be between 0°-360° relative to an X-axis, between 0°-180° relative to a Y-axis, or 0°-180° relative to a Z-axis.

In an exemplary embodiment, the beam assembly includes a flag recess adapted to receive the flag. The beam assembly may include a distal tip adapted to engage the distal opening on the introducer tube. The distal tip may include a rounded distal surface.

In an exemplary embodiment, wherein the flag includes at least one tab. The at least one tab may include at least one inner tab and at least one outer tab. The at least one tab may be a flap biased toward a folded position.

In an exemplary embodiment, the flag includes a pocket disposed at least partially in the flag recess. The pocket may include a least one slit.

In an exemplary embodiment, the flag is a hydrophobic mesh.

In an exemplary embodiment, a method according to the present invention comprises providing a device comprising: a handle; an introducer assembly slidably and rotatably coupled to the handle; a beam assembly coupled to a distal end of the handle; and a flag coupled to the beam assembly, and placing a barrier on the flag, sliding the introducer assembly along the handle from a retracted position to an extended position at least partially covering the beam assembly, and rotating the handle relative to the introducer assembly until the flag and the barrier are wound around the beam assembly.

In an exemplary embodiment, the barrier is an adhesion barrier. In an exemplary embodiment, the adhesion barrier is a Seprafilm.

DETAILED DESCRIPTION

Exemplary embodiments of a barrier application device according to the present invention may be used to retain a barrier and deploy the barrier at a surgical site. In an exemplary embodiment, the barrier may be adapted to adhere to the surgical site to prevent organs and/or tissue from adhering to the surgical site. In an exemplary embodiment, a barrier may be Seprafilm® Adhesion Barrier made by Genzyme Corporation. In another exemplary embodiment, a barrier may be Gynecare Interceed® made by Ethicon, Inc.

Figure 1A:
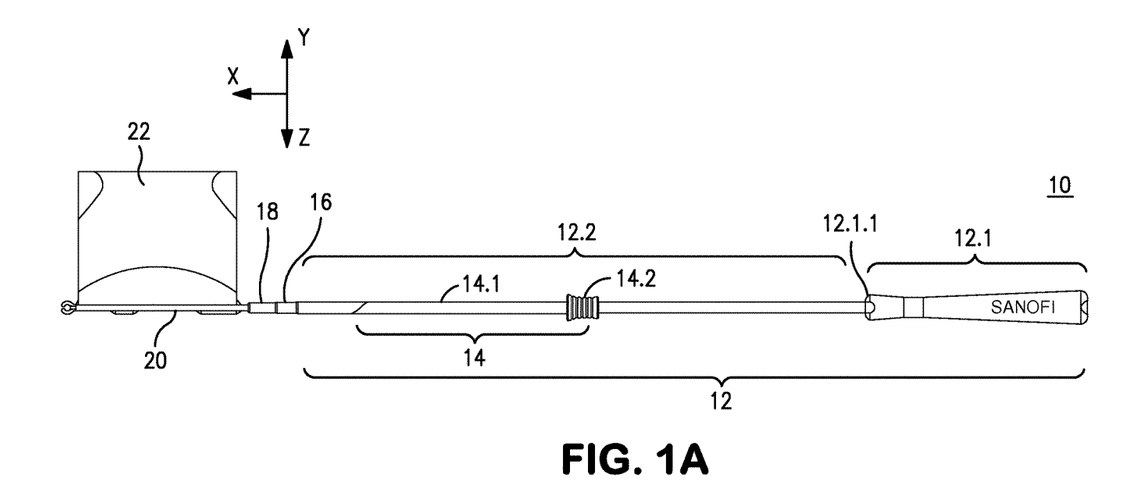
FIG. 1A shows an exemplary embodiment of a barrier application device according to the present invention.
Figure 1B:
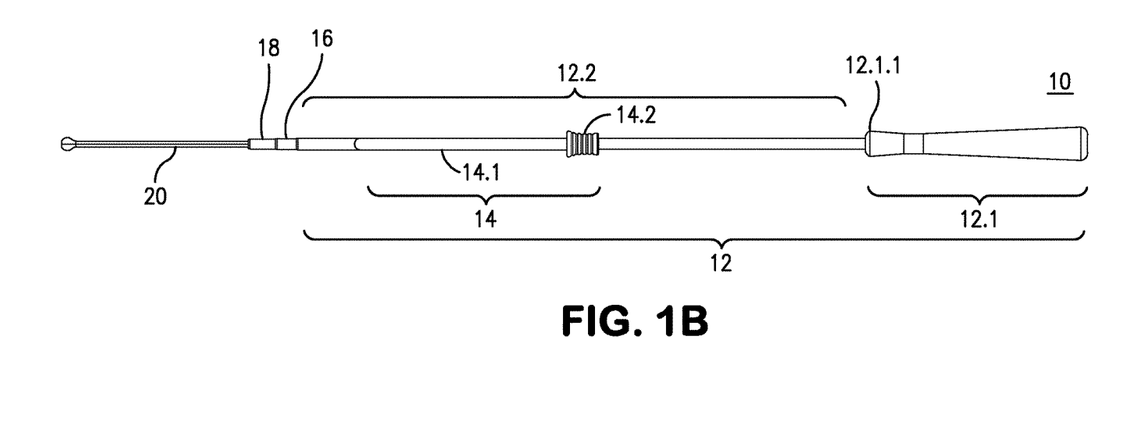
FIG. 1B shows an exemplary embodiment of a barrier application device according to the present invention.

FIGS. 1A and 1B show an exemplary embodiment of a barrier application device 10 according to the present invention. The application device 10 comprises a handle 12 including a grip portion 12.1 and a shaft 12.2 extending therefrom. In an exemplary embodiment, the grip portion 12.1 is ergonomically shaped (e.g., cylindrical, conical, frusto-conical or any combination thereof) for being gripped and handled by a user. In an exemplary embodiment, a gripping surface (not shown), such as a frictional material or an array of projections, may be disposed on the grip portion to enhance the grip of the user and preventing slipping during use. An orientation indicator 12.1.1 may be disposed on the grip portion 12.1. In an exemplary embodiment, the orientation indicator 12.1.1 may be a projection, recess, symbol or any other feature and may have a color different from a color of the grip portion 12.1 to provide visual feedback to the user. The shaft 12.2 extends distally from a distal end of the grip portion 12.1. In an exemplary embodiment the shaft 12.2 is coaxially aligned with the grip portion 12.1. In an exemplary embodiment, the handle 12 is made from acrylonitrile butadiene styrene.

Figure 2:
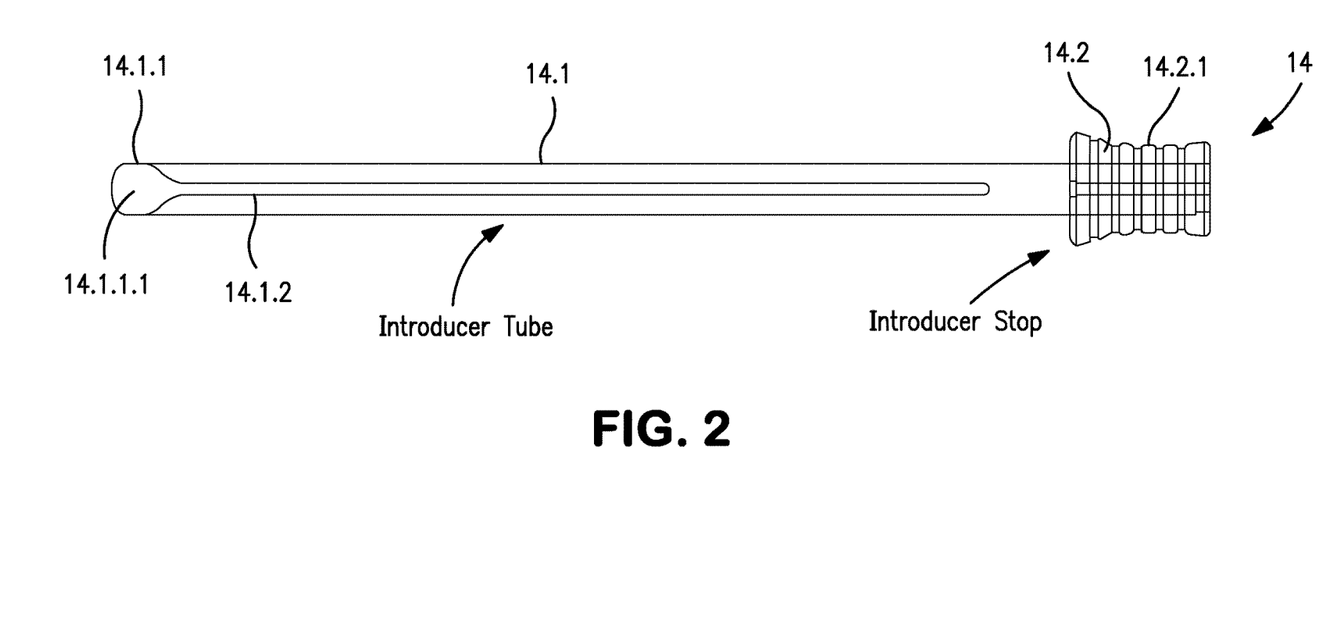
FIG. 2 shows an exemplary embodiment of an introducer assembly for a barrier application device according to the present invention.

An introducer assembly 14 is slidably and rotatably coupled to the handle 12. FIG. 2 shows an exemplary embodiment of the introducer assembly 14 according to the present invention. In an exemplary embodiment, the introducer assembly 14 is slidably coupled to the shaft 12.2 and includes an introducer tube 14.1 and an introducer stop 14.2. In an exemplary embodiment, the introducer tube 14.1 is a hollow cylinder that includes a distal end 14.1.1 that is beveled. The distal end 14.1.1 includes a distal opening 14.1.1.1 which is contiguous with a slot 14.1.2 formed along at least a portion of a length of the introducer tube 14.1. In an exemplary embodiment, the introducer tube 14.1 is made from stainless steel.

In an exemplary embodiment, the introducer stop 14.2 has an outer diameter larger than an outer diameter of the introducer tube 14.1. As explained further below, the introducer stop 14.2 is adapted to abut an insertion device (e.g., a trocar) which provides access to a surgical site. Further, the introducer stop 14.2 may provide one or more features, such as ridges 14.2.1, to enhance a grip and prevent slipping when the user is holding the introducer stop 14.2. In an exemplary embodiment, the introducer stop 14.2 is overmolded on the introducer tube 14.1 and is made from acrylonite butadiene styrene.

As explained further below, the introducer assembly 14 is slidable relative to the shaft 12.2 between a retracted position (shown in FIGS. 1A-B) and an extended position, and the introducer assembly 14 is freely rotatable relative to the shaft 12.2.

Referring back to the exemplary embodiment shown in FIGS. 1A-B, a sleeve 16 is coupled to a distal end of the handle 12. For example, the sleeve 16 may be disposed on a distal end of the shaft 12.2 to prevent the introducer 14 from sliding distally off the distal end of the shaft 12.2. In an exemplary embodiment, the sleeve 16 may be made from polypropylene.

In an exemplary embodiment, a flex joint 18 may be coupled to a distal end of the shaft 12.2. In an exemplary embodiment, the flex joint 18 may be a cylindrical element having a proximal female end adapted to engage a distal end of the shaft 12.2 and a distal female end adapted to engage a proximal end of a beam assembly 20. In an exemplary embodiment, the distal end of the shaft 12.2 and/or the proximal end of the beam assembly 20 may include one or more barbs adapted to engage the proximal and distal ends, respectively, of the flex joint 18. The distal end of the shaft 12.2 and/or the proximal end of the beam assembly 20 may include one or more holes or recesses (radially or axially formed) to receive a corresponding projection(s) on the flex joint 18 (e.g., when the flex joint 18 is being molded). In another exemplary embodiment, the flex joint 18 may be inserted into an open distal end of the sleeve 16. The flex joint 18 may be biased in a non-deflected state (shown in FIGS. 1A-B) in which the flex joint 18 is coaxially aligned with the shaft 12.2. When a force is applied, the flex joint 18 may be capable of bending 360° around the X-axis and approximately 180° around the Y-axis, and approximately 180° around the Z-axis. When the force is removed, the flex joint 18 may return to the non-deflected state. In an exemplary embodiment, the flex joint 18 is made from thermoplastic elastomer. In an exemplary embodiment, a tensile strength of the flex joint 18 is greater than approximately 9.1N.

Figure 3:
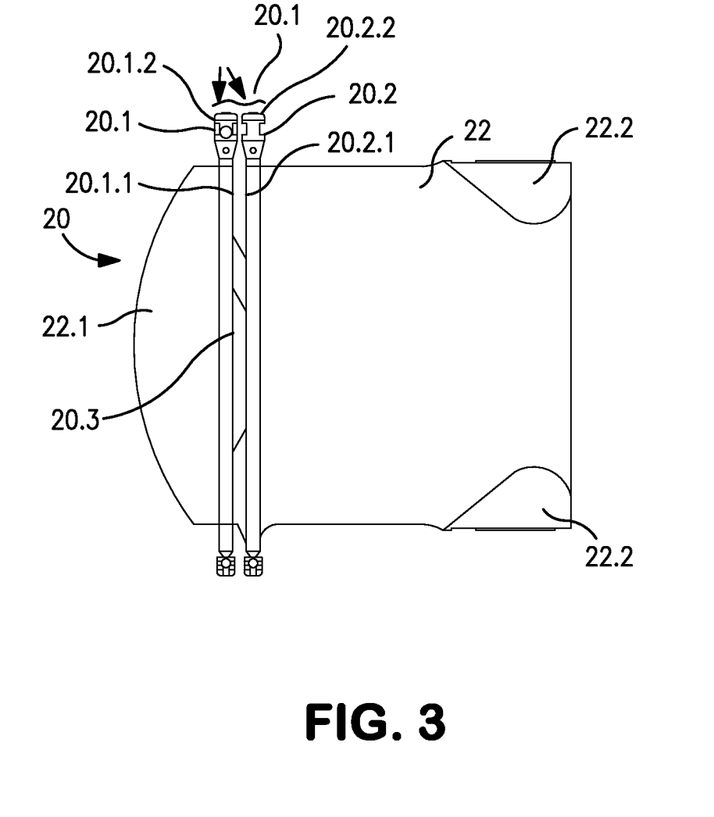
FIG. 3 shows an exemplary embodiment of a beam assembly and a flag for a barrier application device according to the present invention.

In art exemplary embodiment, a beam assembly 20 is coupled to the flex joint 18 and a flag 22 is coupled to the beam assembly 20. FIG. 3 shows an exemplary embodiment of the beam assembly 20 according to the present invention. In an exemplary embodiment, the beam assembly 20 comprises a first beam 20.1 and a second beam 20.2. In an exemplary embodiment, the first beam 20.1 has a semi-circular cross-section, and the second bean 20.2 has a complementary semi-circular cross-section. When the first beam 20.1 is coupled to the second beam 20.2, an axial space is formed between the beams 20.1, 20.2 which acts as a flag recess 20.3 in which the flag 22 is disposed.

In an exemplary embodiment, the first beam 20.1 includes a first distal tip 20.1.2, and the second beam 20.2 includes a second distal 20.2.2. In an exemplary embodiment, each of the first and second distal tips 20.1.2, 20.2.2 is substantially semi-spherical or a halved tear-drop. When the first beam 20.1 is coupled to the second beam 20.2, the first distal tip 20.1.2 and the second distal tip 20.2.2 are axially aligned to form a distal tip 20.4. In an exemplary embodiment, at least a portion of the distil tip 20.4 may be received by the distal opening 14.1.1.1 when the introducer assembly 14 is in the extended position. In an exemplary embodiment, the first and second beams 20.1, 20.2 are made from acrylonite butadiene styrene. In an exemplary embodiment, the orientation indicator 12.1.1 may be disposed on the first beam 20.1 and/or the second beam 20.2. For example, one of the beams could be a different color or include a symbol.

FIG. 3 shows an exemplary embodiment of a flag 22 according to the present invention. In an exemplary embodiment, the flag 22 is substantially rectangular and includes an inner tab 22.1 and at least one outer tab 22.2 spaced radially from the inner tab 22.1. As explained further below, the flag 22 is adapted to receive a barrier, and the tabs 22.1, 22.2 are adapted to retain the barrier against the flag 22 until the barrier is deployed. In an exemplary embodiment, the inner tab 22.1 is adapted to fold about the X-axis and the at least one outer tab 22.2 is adapted to fold about the Z-axis. In an exemplary embodiment, the tabs 22.1, 22.2 are flaps that are biased toward a folded position to engage a barrier when placed on a surface of the flag 22. The tabs 22.1, 22.2 can be opened to an open position to receive the barrier. In an exemplary embodiment, one or more slits 22.4 may be formed (e.g., cut) between the inner tab 22.1 and the flag 22. As explained further below, during assembly, the inner tab 22.1 may be folded along the at least one slit 22.3 toward the at least one outer tab 22.2 to create a pocket for receiving the barrier. In an exemplary embodiment, the flag 22 is made from a hydrophobic polyester mesh. The mesh and the hydrophobic material may prevent surface tension from adhering to the barrier B, and the hydrophobic material may further help shed water and blood from the flag 22 that may be encountered during the surgical procedure. In an exemplary embodiment, the orientation indicator 12.1.1 may be disposed on the flag 22 as, for example, text or a symbol.

In an exemplary embodiment of manufacturing and assembling the application device 10, the handle 12 is injection molded. The introducer tube 14.1 is made and the introducer stop 14.2 is overmolded thereon to form the introducer assembly 14. The introducer assembly 14 is then coupled to the handle 12 by sliding the introducer assembly 14 onto the shaft 12.2. The sleeve 16 is then coupled to the distal end of the shaft 12.2.

The flag 22 is made from a polyester mesh which is laser cut into a predetermined shape (e.g., including the tabs and slits). The first and second beams 20.1 and 20.2 are overmolded on to portions of the flag 22, as shown in FIG. 3. For example the first beam 20.1 may be molded on a first side of the slit 22.3, and the second beam 20.2 may be molded on a second side of the slit 22.3. The inner tab 22.1 may be folded toward the outer tab 22.2 to create a pocket 22.3 (shown in FIG. 4), and the first and second beams 20.1, 20.2 are coupled together (e.g., via a snap-fit, friction fit, latch, hook, etc.).

The beam assembly 20 with the flag 22 is placed with the handle/introducer/sleeve assembly into a mold for the flex joint 18. The flex joint 18 is then overmolded onto a distal portion of the sleeve 16 and a proximal portion of the beam assembly 20.

The fully assembled application device 10 may then be placed in a sterile enclosure.

Figure 4:
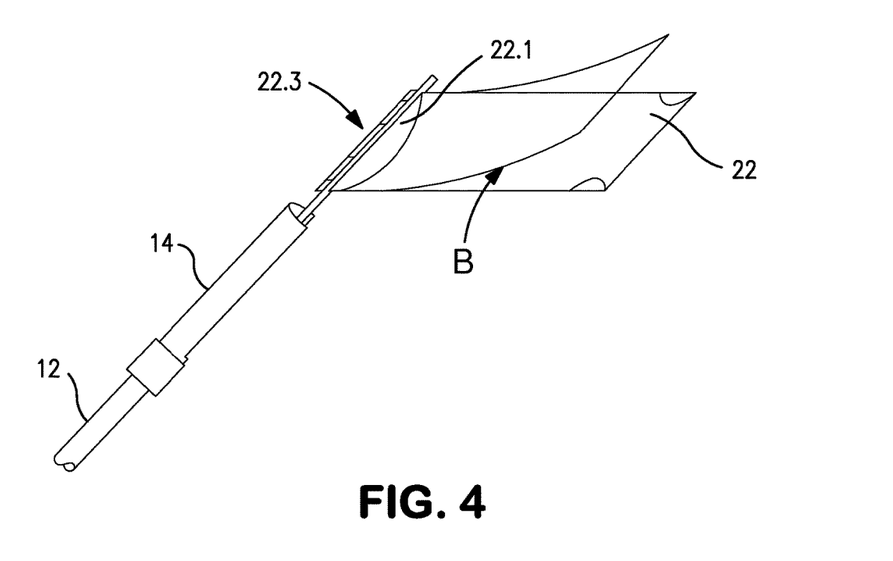
FIG. 4 shows an exemplary embodiment of a barrier application device according to the present invention prior to use.

FIGS. 4-9 shows an exemplary embodiment of a use of a barrier application device 10 according to the present invention. As shown in FIG. 4, the introducer assembly 10 is in a retracted position relative to the beam assembly 20 so that the beam assembly 20 is exposed. A proximal end of the introducer tube 14.1 may abut a distal end of the grip portion 12.1 of the handle 12 as a proximal stop. A barrier B may be placed on the flag 22 such that a first lateral edge of the barrier B is inserted into the pocket 22.3 under the inner tab 22.1. The one or more slits 22.4 may provide a visual feedback that the first lateral edge of the barrier B has been properly inserted through the first and second beams 20.1, 20.2 and into the pocket 22.3.

Figure 5:
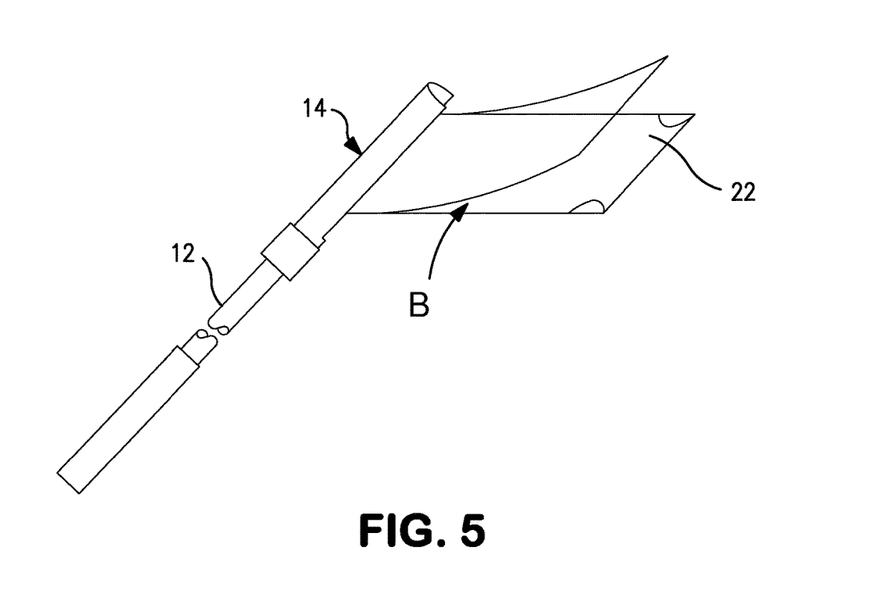
FIG. 5 shows an exemplary embodiment of a barrier application device according to the present invention prior to use.

As shown in FIG. 5, the introducer assembly 14 is moved from the retracted position to the extended position. The introducer assembly 14 may be rotated so that the slot 14.1.2 aligns with the flag recess 20.3 in the beam assembly 20. As the introducer assembly 14 moves from the retracted position to the extended position, the slot 14.1.2 may receive the flag 22 and the barrier B thereon. In an exemplary embodiment, the beveled distal end 14.1.1 of the introducer tube 14.1 may facilitate the alignment of the slot 14.1.2 and the flag recess 20.3 such that the flag 22 (and the barrier B thereon) will not be crimped or folded by an impact of the introducer tube 14.1 and the flag 22. That is, the impact of the flag 22 on the beveled distal end 14.1.1 may induce rotation of the introducer assembly 14 to align the slot 14.1.2 and the flag recess 20.3. In an exemplary embodiment, a distal end of the introducer stop 14.2 may abut a proximal end of the sleeve 16 to define the extended position of the introducer assembly 14. In another exemplary embodiment, the distal tip 20.4 may have a larger cross-section than the distal end 14.1.1 of the introducer tube 14, and the distal end 14.1.1 of the introducer tube 14 may abut the distal tip 20.4 of the beam assembly 20 to define the extended position. In this exemplary embodiment, the distal tip 20.4 may provide a bearing surface for rotation of the introducer tube 14. In the extended position, a distal surface of the beveled portion of the distal end 14.1.1 may be proximal of a distal surface of the distal tip 20.4 of the beam assembly 20. This may prevent the beveled edge from damaging tissue/organ when inserted into the surgical site.

Figure 6:
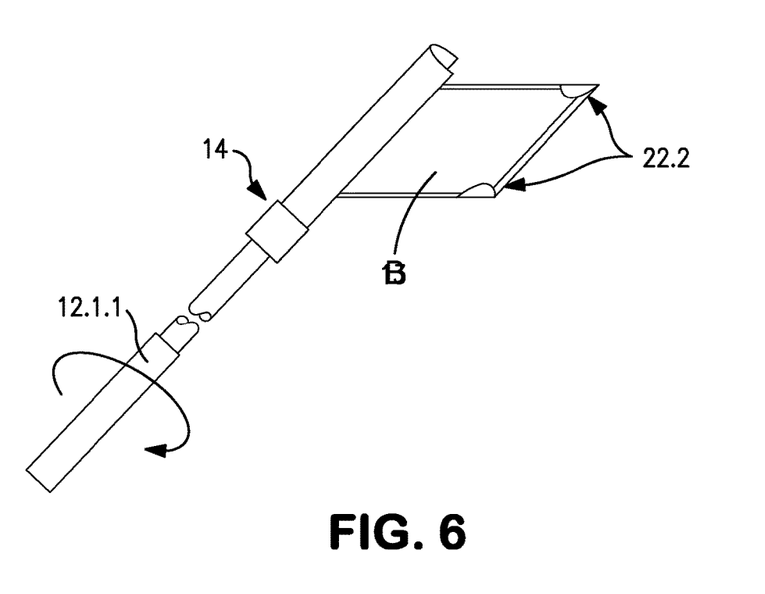
FIG. 6 shows an exemplary embodiment of a barrier application device according to the present invention prior to use.

As shown in FIG. 6, when the introducer assembly 14 is in the extended position, the handle 12 is rotated relative to the introducer assembly 14 which causes the flag 22 and the barrier B to roll around the beam assembly 20. In an exemplary embodiment, a second lateral edge of the barrier B may be inserted beneath the at least one outer tab 22.2, and the flag 22 and barrier B may be rolled until they are no longer visible out of the slot 14.1.2. As the handle 12 is rotated relative to the introducer assembly 14, at least one of the beams 20.1, 20.2 engage the barrier B, which prevents the barrier B from disengaging the flag 22. In another exemplary embodiment, an adhesive could be disposed on the flag 22 and/or at least one of the beams 20.1, 20.2 to engage the barrier B. In yet another exemplary embodiment, at least one of the beams 20.1, 20.2 may include a barb adapted to engage the barrier B.

When the flag 22 and the barrier B are substantially retained in the introducer assembly 14, the application device 10 may be deployed to the surgical site and the introducer assembly 14 may be moved from the extended position to the retracted position. In an exemplary embodiment, when the application device 10 is deployed to the surgical site, it is inserted into a trocar, and the introducer stop 14.2. abuts a portion of the trocar which causes the introducer assembly 14 to retract as the handle 12 is inserted distally toward the surgical site.

Figure 7:
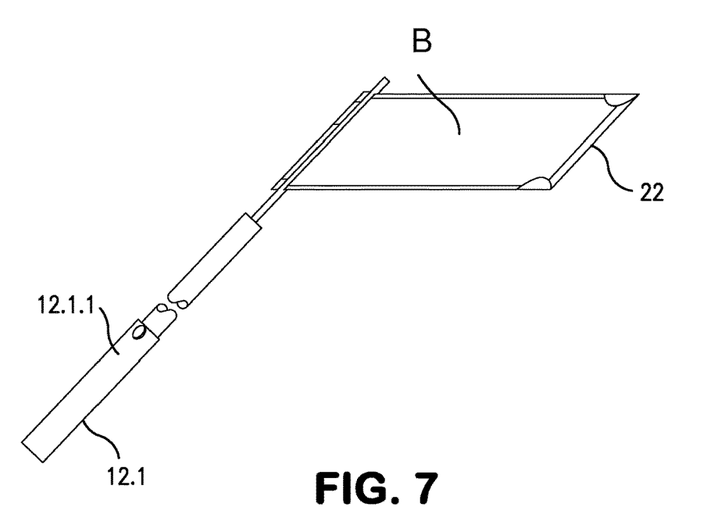
FIG. 7 shows an exemplary embodiment of a barrier application device according to the present invention during use.

As shown in FIG. 7, the introducer assembly 14 is in the retracted position, and the flag 22 and the barrier B may at least partially unravel. The orientation indicator 12.1.1 provides a visual feedback regarding the orientation of the flag 22 and the barrier B. For example, the position of the orientation indicator 12.1.1 on the grip portion 12.1 may indicate a position in which an exposed surface of the barrier B is oriented.

Figure 8:
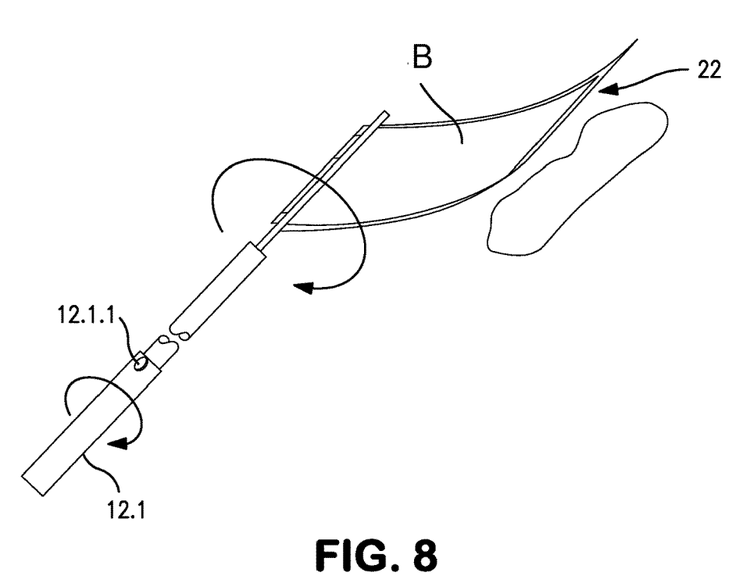
FIG. 8 shows an exemplary embodiment of a barrier application device according to the present invention during use.

As shown in FIG. 8, the handle 12 may be rotated to align the barrier B with the surgical site. The flag 22 prevents a non-exposed surface of the barrier B from adhering to an organ or tissue as the handle 12 is rotated. Further, the beam assembly 20 may be deflected via the flex joint 18 to properly orient and position the harder B. A rounded distal surface of the distal tip 20.4 may prevent trauma to organs and/or tissue during use of the application device 10.

Figure 9:
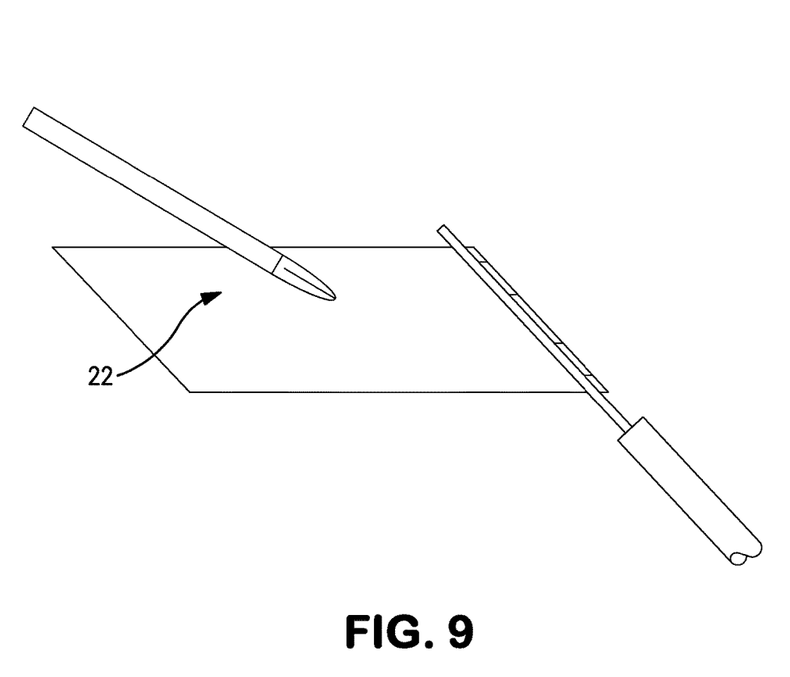
FIG. 9 shows an exemplary embodiment of a barrier application device according to the present invention during use.

As shown in FIG. 9, when the barrier B is applied to the surgical site, a further surgical tool may be used to manipulate the barrier B, e.g., to ensure that it adheres to the surgical site.

After the barrier B has been deployed, the handle 20 is pulled proximally relative to the introducer assembly 14, and the handle 20 is rotated until the flag 22 is substantially within the introducer assembly 14 and can be removed from the surgical site.

In an exemplary embodiment, an unused barrier may be applied to the flag 22 and the application device 10 may be reused.

In another exemplary embodiment, the shaft 12.1 may include one or more projections adapted to engage the introducer tube 14.1. The projections may prevent free sliding of the introducer assembly 14 relative to the shaft 12.1 and/or provide tactile feedback (e.g., resistance) when inserting the application device 10 into a trocar.

While the exemplary embodiments of the application device have been described with respect to a barrier, those of skill in the art will understand that other materials may be retained and deployed by the application device according to the present invention. For example, gauze, a sponge, or any other thin, flexible material may be retained and deployed by the application device of the present invention in a manner similar to as described above with respect to a barrier.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A device comprising:
    a handle;
    an introducer assembly slidably and rotatably coupled to the handle, wherein the introducer assembly includes an introducer tube having a wall surrounding a hollow cavity with a distal opening that is contiguous with a slot formed in the wall along at least a portion of a length of the introducer tube;
    a beam assembly coupled to a distal end of the handle and configured to slide within the hollow cavity of the introducer tube, wherein the beam assembly includes a first beam having a first longitudinal axis and a second beam having a second longitudinal axis parallel to the first longitudinal axis; and
    a flag configured to receive an implantable adhesion barrier and coupled to the beam assembly, wherein the hollow cavity is configured to receive the flag when the flag is wound around the beam assembly and the slot is configured to receive the flag when the flag is at least partially unwound from around the beam assembly.

2. The device according to claim 1, wherein the handle includes a grip portion and a shaft portion.

3. The device according to claim 2, wherein the grip portion includes an orientation indicator.

4. The device according to claim 3, wherein the orientation indicator includes at least one of a projection, a recess, a symbol and a color.

5. The device according to claim 1, wherein the introducer tube has a distal end that is beveled.

6. The device according to claim 5, wherein the beam assembly includes a distal tip adapted to engage the distal opening on the introducer tube.

7. The device according to claim 6, wherein the distal tip includes a rounded distal surface.

8. The device according to claim 1, wherein the beam assembly includes a flag recess adapted to receive the flag, wherein the flag recess includes an axial space formed between the first longitudinal axis of the first beam and the second longitudinal axis of the second beam.

9. The device according to claim 8, wherein the flag includes a pocket disposed at least partially in the flag recess.

10. The device according to claim 9, wherein the pocket includes a least one slit.

11. The device according to claim 1, wherein the flag includes at least one tab.

12. The device according to claim 11, wherein the at least one tab includes at least one inner tab and at least one outer tab.

13. The device according to claim 11, wherein the at least one tab is a flap biased toward a folded position.

14. The device according to claim 1, further comprising:
    a flex joint coupled to the beam assembly and the handle, the flex joint being biased in a non-deflected state coaxial with the handle and movable to a deflected state at an angle relative to the handle.

15. The device according to claim 14, wherein the angle is between 0° -360° relative to an X-axis, between 0°-180° relative to a Y-axis, or 0°-180° relative to a Z-axis.

16. The device according to claim 1, wherein the introducer assembly includes an introducer stop having an external diameter greater than an external diameter of the introducer tube.

17. The device according to claim 1, further comprising:
    a sleeve coupled to a distal end of the handle.

18. The device according to claim 1, wherein the flag is a hydrophobic mesh.

19. The device according to claim 1, wherein the flag is flexible and the first and second beams are non-flexible.

20. The device according to claim 1, wherein the first beam has a distal first beam end and the second beam has a distal second beam end coupled to the distal first beam end.

21. The device according to claim 1, wherein the first beam has a semi-circular cross section and the second beam has a complementary semi-circular cross section.

22. The device according to claim 1, wherein the flag is substantially rectangular and the first and second beams are linear along their entire length.

23. A method comprising:
    providing a device comprising:
        a handle;
        an introducer assembly slidably and rotatably coupled to the handle, wherein the introducer assembly includes an introducer tube having a wall surrounding a hollow cavity with a distal opening that is contiguous with a slot formed in the wall along at least a portion of a length of the introducer tube;
        a beam assembly coupled to a distal end of the handle and configured to slide within the hollow cavity of the introducer tube, wherein the beam assembly includes a first beam having a first longitudinal axis and a second beam having a second longitudinal axis parallel to the first longitudinal axis; and
        a flag coupled to the beam assembly;
    placing a barrier on the flag when the flag is substantially planar;
    sliding the introducer assembly along the handle from a retracted position to an extended position at least partially covering the beam assembly and locating the flag within the slot; and rotating the handle relative to the introducer assembly until the flag and the barrier are wound around the beam assembly and located within the hollow cavity.

24. The method according to claim 23, wherein the barrier is an adhesion barrier.

\* \* \* \* \*